US010264794B2

(12) United States Patent
Murray

(10) Patent No.: US 10,264,794 B2
(45) Date of Patent: Apr. 23, 2019

(54) COMPOSITIONS COMPRISING UNSATURATED FATTY ESTERS AND USES THEREOF

(71) Applicant: Stella-Jones Inc., Saint Laurent (CA)

(72) Inventor: Gordon Murray, North River (CA)

(73) Assignee: Stella-Jones Inc., Saint-Laurent (CA)

( * ) Notice: Subject to any disclaimer, the term of this patent is extended or adjusted under 35 U.S.C. 154(b) by 778 days.

(21) Appl. No.: 14/769,992

(22) PCT Filed: Mar. 6, 2014

(86) PCT No.: PCT/IB2014/001005
§ 371 (c)(1),
(2) Date: Aug. 24, 2015

(87) PCT Pub. No.: WO2014/140854
PCT Pub. Date: Sep. 18, 2014

(65) Prior Publication Data
US 2016/0000090 A1 Jan. 7, 2016

Related U.S. Application Data

(60) Provisional application No. 61/784,541, filed on Mar. 14, 2013.

(51) Int. Cl.
| | | |
|---|---|---|
| *A01N 61/02* | (2006.01) | |
| *C08L 95/00* | (2006.01) | |
| *A01N 31/10* | (2006.01) | |
| *B27K 3/08* | (2006.01) | |
| *E01B 3/02* | (2006.01) | |
| *E04H 12/04* | (2006.01) | |
| *B27K 3/34* | (2006.01) | |
| *B27K 3/46* | (2006.01) | |
| *C08L 91/00* | (2006.01) | |

(52) U.S. Cl.
CPC ............ *A01N 61/02* (2013.01); *A01N 31/10* (2013.01); *B27K 3/08* (2013.01); *C08L 95/00* (2013.01); *E01B 3/02* (2013.01); *E04H 12/04* (2013.01); *B27K 3/34* (2013.01); *B27K 3/46* (2013.01); *C08L 91/00* (2013.01)

(58) Field of Classification Search
None
See application file for complete search history.

(56) References Cited

U.S. PATENT DOCUMENTS

| | | | |
|---|---|---|---|
| 2,051,486 A | 8/1936 | Kautter et al. | |
| 2,182,081 A | 12/1939 | Hatfield | |
| 2,789,060 A * | 4/1957 | Spangenberg | A01N 25/02 106/18 |
| 3,518,348 A | 6/1970 | Dulat | |
| 3,574,855 A | 4/1971 | Brown | |
| 3,600,408 A | 8/1971 | Bursack et al. | |
| 3,881,940 A * | 5/1975 | Amundsen | A01N 31/10 106/1.14 |
| 3,956,100 A | 5/1976 | Todd | |
| 3,960,969 A | 6/1976 | Greco et al. | |
| 4,051,282 A | 9/1977 | Davies | |
| 4,076,871 A | 2/1978 | Short et al. | |
| 4,234,665 A | 11/1980 | Johnson | |
| 4,461,721 A | 7/1984 | Goettsche et al. | |
| 4,585,795 A | 4/1986 | Linderborg | |
| 4,929,454 A | 5/1990 | Findlay et al. | |
| 5,078,912 A | 1/1992 | Goettsche et al. | |
| 5,080,935 A | 1/1992 | Kelso et al. | |
| 5,098,472 A | 3/1992 | Watkins et al. | |
| 5,104,664 A | 4/1992 | Vincent et al. | |
| 5,246,652 A | 9/1993 | Hsu et al. | |
| 5,296,240 A | 3/1994 | Vincent et al. | |
| 5,447,686 A | 9/1995 | Seidner | |
| 5,460,816 A | 10/1995 | Palmere et al. | |
| 5,641,726 A | 6/1997 | Walker | |
| 5,645,828 A | 7/1997 | Palmere et al. | |
| 5,700,841 A | 12/1997 | Walker | |
| 5,709,821 A | 1/1998 | Von Bonin et al. | |
| 5,891,921 A | 4/1999 | Walker | |
| 5,958,463 A | 9/1999 | Milne et al. | |
| 6,087,303 A | 7/2000 | Walker | |
| 6,103,387 A | 8/2000 | Yamamoto et al. | |
| 6,426,095 B2 | 7/2002 | Palmere et al. | |
| 6,630,174 B2 | 10/2003 | Palmere et al. | |
| 6,953,501 B2 | 10/2005 | Kelley et al. | |
| 7,597,902 B2 | 10/2009 | Lloyd et al. | |

(Continued)

FOREIGN PATENT DOCUMENTS

| | | |
|---|---|---|
| CA | 1306663 | 8/1992 |
| CA | 2726795 | 7/2012 |

(Continued)

OTHER PUBLICATIONS

Landgroodi et al. S96: Bioremoval of Pentachlorophenol (PCP) in biodiesel versus diesel carriers, SIM Annual Meeting and Exhibition, Jul. 26, 2011.

Lebow et al., USDA Forest Service Research Note FPL-RN-0295, 6 pp. (Apr. 2005).

Lesar et al., Performance of Boron-ethanolamine-quaternary Ammonium Based Wood Preservatives Against Leaching, Wood Decay and Blue Stain Fungi, Wood Research, 2008, vol. 53, No. 3, p. 17-26.

Roll, D., "Wood Preservation Category 4b, Study Guide for Commercial Applicators," Ohio Department of Agriculture—Pesticide Regulation—Certificate and Training, Aug. 2016, pp. 1-59, XP055074601.

(Continued)

*Primary Examiner* — Chinessa T. Golden
(74) *Attorney, Agent, or Firm* — Foley & Lardner LLP

(57) ABSTRACT

Disclosed is a wood preservative composition comprising creosote and/or pentachlorophenol (PCP) and one or more unsaturated fatty esters. The composition is useful for reducing insect and microbial decay in wood. Further disclosed are methods of making and using such a composition and wood treated with such a composition.

26 Claims, No Drawings

(56) References Cited

U.S. PATENT DOCUMENTS

| | | |
|---|---|---|
| 8,465,780 B2 | 6/2013 | Lloyd |
| 8,709,462 B2 | 4/2014 | Lloyd et al. |
| 9,644,103 B2 | 5/2017 | Murray |
| 9,681,660 B2 | 6/2017 | Murray |
| 9,808,955 B2 | 11/2017 | Murray |
| 2003/0121445 A1 | 7/2003 | Herbert et al. |
| 2003/0213400 A1 | 11/2003 | Thompson |
| 2004/0028934 A1 | 2/2004 | Preston et al. |
| 2005/0013939 A1 | 1/2005 | Vinden et al. |
| 2005/0186352 A1 | 8/2005 | Hutter et al. |
| 2006/0086841 A1* | 4/2006 | Richardson et al. ........... 241/30 |
| 2007/0151476 A1 | 7/2007 | Humar et al. |
| 2008/0221067 A1 | 9/2008 | Hoffman |
| 2009/0069271 A1 | 3/2009 | Stanimiroff |
| 2010/0297204 A1 | 11/2010 | Uhr et al. |
| 2011/0039031 A1 | 2/2011 | Cobham et al. |
| 2012/0121445 A1 | 5/2012 | Lee et al. |
| 2012/0171504 A1 | 7/2012 | Murray |

FOREIGN PATENT DOCUMENTS

| | | |
|---|---|---|
| GB | 0 249 698 | 4/1926 |
| WO | WO-2009/129587 | 10/2009 |
| WO | WO-2014/140854 | 9/2014 |

OTHER PUBLICATIONS

International Search Report and Written Opinion regarding International Appl. No. PCT/IB2014/001005, dated Sep. 2, 2014, 8 pages.

Webb et al., 1958 Cooperative Creosote Project-XIV: 35 Years of Field Experience with Posts, AWPA Proceedings, 1995, vol. 91, pp. 120-125.

International Search Report and Written Opinion regarding International Appl. No. PCT/IB2015/051561, dated Jun. 25, 2015, 9 pages.

* cited by examiner

COMPOSITIONS COMPRISING UNSATURATED FATTY ESTERS AND USES THEREOF

CROSS REFERENCE TO RELATED APPLICATIONS

This application claims priority to and the benefit of U.S. Provisional Application Ser. No. 61/784,541, filed on Mar. 14, 2013, and entitled COMPOSITIONS COMPRISING UNSATURATED FATTY ESTERS AND USES THEREOF, the disclosure of which is herein incorporated by reference in its entirety.

BACKGROUND OF THE INVENTION

Wood products have been used as utility poles, railway ties, and construction materials in a wide variety of industries. Without proper treatment, wood products deteriorate and are susceptible to weathering, insects (e.g., termites, carpenter ants, and beetles), marine borers (e.g., mollusks and crustaceans), bacteria, and fungi (e.g., stains, white rot, soft rot, and brown rot). Wood treatment is required to prevent these problems. More effective wood treatment compositions are needed.

Preservatives used to treat wood, such as creosote and pentachlorophenol (PCP) containing compositions are effective at preserving wood, but may emit naphthalene and other volatile organic compounds (VOCs) that are associated with petroleum and coal tar distillates. Some of these volatile compounds are toxic and/or have unpleasant odors. In particular, these VOCs are both a health risk and a nuisance for the plants using either creosote or PCP in diesel carrier oil.

During wood-treatment processes, creosote-based or PCP/diesel-based preservatives are brought to elevated temperatures and the VOCs are released to the atmosphere. Consequently, many plants are required to install expensive air scrubbers and incineration units which have a high capital cost. Further, the sequestered VOCs must be contained and disposed, further adding to production costs and potential hazards.

The VOCs also tend to persist in the treated wood products and off-gas from the wood products over time. This gradual emission of VOCs from treated wood yields unpleasant odors that are not suitable for populated areas. As such, more active and effective odor suppressants are needed. The discovery of more active odor suppressants will yield wood preservative compositions that are more concentrated in creosote and/or PCP/diesel without the unacceptably high levels of odors and VOCs that are currently attributed to these chemicals.

SUMMARY OF THE INVENTION

The creosote-based and PCP/diesel-based wood preservative formulations described herein contain unsaturated fatty esters in relatively pure form (e.g., greater than 80 wt %, 90 wt %, 95 wt %, 98 wt % or 99 wt %) and are a significant advance over existing formulations because the inventive formulations described herein exhibit a reduced odor and emit a reduced quantity of VOCs, such as naphthalene during the wood treatment process at high temperature. Also, the wood products, such as utility poles and railroad ties, that are treated with the compositions described herein, exhibit little odor and emit a reduced quantity of VOCs throughout the lifespan of the wood product.

In one aspect, a composition is provided, where the composition comprises i) 85 wt % to about 99 wt % creosote; and ii) 1 wt % to about 15 wt % of one or more $C_{10}$-$C_{50}$ unsaturated fatty esters.

In another aspect, a composition is provided, where the composition comprises i) 1 wt % to about 20 wt % pentachlorophenol (PCP); ii) 65 wt % to about 98 wt % diesel; and iii) 1 wt % to about 15 wt % of one or more $C_{10}$-$C_{50}$ unsaturated fatty esters.

In some embodiments, any of the compositions described herein comprises 3 wt % to about 10 wt % of the one or more $C_{10}$-$C_{50}$ unsaturated fatty esters. In other embodiments, the composition is substantially free of biodiesel. In further embodiments, the composition is substantially free of $C_{10}$-$C_{50}$ saturated fatty esters.

In some embodiments, any of the compositions described herein further comprises a borate compound. In some embodiments, the borate compound is an ester of boric acid.

In another aspect, a method is provided of treating wood, comprising the steps of: a) immersing the wood in the treatment solution comprising any one of the compositions described herein; and b) pressure impregnating the immersed wood above 1 atm (101.325 kPa).

In another aspect, a method is provided of minimizing odor in treated wood, comprising the steps of: a) immersing the wood in the treatment solution comprising any one of the compositions described herein; and b) pressure impregnating the immersed wood above 1 atm (101.325 kPa).

In yet another aspect wood is provided, wherein the wood is coated with or immersed in any one of the compositions described herein. In some embodiments, the wood is a utility pole. In some embodiments, the wood is a railroad tie. In some embodiments, the wood is treated according to any of the methods described herein.

DETAILED DESCRIPTION OF THE INVENTION

Biodiesel has been used as an odor suppressing additive in creosote and pentachlorophenol (PCP) containing compositions for the treatment of wood. However, preservative formulations generally require significant quantities of biodiesel to yield appreciable reductions in odor.

For example, in some existing creosote-based wood preservative formulations, up to 45 wt/wt % biodiesel is necessary to reduce the odor of these formulations to acceptable levels. Further, in some PCP/diesel-based wood preservative formulations, up to 38 wt/wt % biodiesel is necessary to reduce the odor of these formulations to acceptable levels.

Such high concentrations of biodiesel, dilute the efficacy of creosote-based and PCP/diesel-based wood preservative formulations. Biodiesel is especially problematic in creosote-based formulations because biodiesel, especially at high concentrations, lowers the viscosity and specific gravity of creosote. This compromises the ability of creosote to (a) seal the wood and act as a physical barrier between the atmosphere and the interior of the wood and (b) impart load carrying enhancements to the treated wood structure. In other words, a railroad tie treated with pure creosote will generally have a higher load-carrying ability than a similar tie treated with creosote diluted with biodiesel. The creosote diluted with biodiesel has a lower viscosity and specific gravity.

It has now been discovered that low levels (e.g., about 0.1 to about 20% of unsaturated fatty esters are remarkably effective at sequestering VOCs in creosote-based and PCP/diesel-based wood preservative formulations. Because only low concentrations of these unsaturated fatty esters are needed to sequester VOCs and reduce odor, the resulting creosote-based and PCP/diesel-based wood preservative formulations are more concentrated in wood preservatives than biodiesel-based formulations.

Some of the unsaturated fatty esters that are included in the compositions described herein are constituents of some biodiesel formulations, such as soy-based or linseed-based biodiesel. However, it has been surprisingly discovered, that the unsaturated fatty esters, when used in relatively pure form, are far more effective at sequestering VOCs and reducing odor, than the complex mixture of compounds in biodiesel, including soy-based or linseed-based biodiesel. Over the course of developing the technology described herein, it has been discovered that biodiesel formulations contain numerous compounds, such as saturated fatty esters, other natural products and side-products of biodiesel production, that do not effectively sequester VOCs or reduce odor. Consequently, high quantities of biodiesel, such as soy-based and linseed-based biodiesel are required to reduce odor in creosote-based or PCP-based wood preservatives.

Creosote-based Compositions

Creosote is a distillate obtained from tars produced from the carbonization of bituminous coal and is a mixture of over three hundred chemicals such as polycyclic aromatic hydrocarbons (PAHs), phenol and cresols created by high temperature treatment of coal. Creosote is commonly used as a biocide to coat wood and protect it from soft rot fungi and to prevent leaching of boron from the interior.

In one aspect, a composition is provided, where the composition comprises i) 85 wt % to about 99 wt % creosote; and ii) 1 wt % to about 15 wt % of one or more $C_{10}$-$C_{50}$ unsaturated fatty esters.

In some embodiments, the any of the creosote-containing compositions has about 85 wt % to about 90 wt % of the creosote. In some embodiments, the any of the creosote-containing compositions has about 90 wt % to about 97 wt % of the creosote. In some embodiments, the any of the creosote-containing compositions has about 90 wt %, 91 wt %, 92 wt %, 93 wt %, 94 wt %, 95 wt %, 96 wt %, 97 wt %, 98 wt %, 99 wt % of the creosote. In any of the above embodiments, the creosote can be combined with any of the unsaturated fatty esters as described herein. In some embodiments, the creosote can be combined with any of the unsaturated fatty esters described herein and any of the borates or esters of boric acid described herein.

PCP/Diesel-based Compositions

Pentachlorophenol (PCP) is an aromatic alcohol that has been used as a broad spectrum biocide in many applications. These include uses as an insecticide, bactericide, herbicide, algicide and molluscide. Pentachlorophenol is an effective biocide due, in part, to its ability to inhibit oxidative phosphorylation by making cell membranes more permeable to protons. This results in a change in the cell's electrical potential.

In its raw form, PCP is crystalline and yellow to brown in color. It is generally used industrially as large blocks of approximately 2,000 kg or as bags of small pellets, each about 1 to about 2 g in weight. Industrial grade PCP can be produced, for example, by the chlorination of phenol or by the hydrolysis of hexachlorobenzene. Industrial grade PCP may contain contaminants, such as chlorophenol isomers (e.g., trichlorophenol or tetrachlorophenol), predioxins, isopredioxins, dioxins, and furans. Certain grades of PCP may contain as little as from about 85% to about 95% PCP. In certain embodiments, technical grade PCP is at least 97% pure. (e.g., PCP from Vulcan Chemicals Inc, Birmingham Ala.) In certain embodiments, the PCP is converted to a phenolate salt such as sodium pentachlorophenate (NaPCP).

In another aspect, a composition is provided, where the composition comprises i) 1 wt % to about 20 wt % pentachlorophenol (PCP); ii) 65 wt % to about 98 wt % diesel; and iii) 1 wt % to about 15 wt % of one or more $C_{10}$-$C_{50}$ unsaturated fatty esters.

In certain embodiments, the composition comprises about 1 wt % to about 15 wt % PCP. In certain embodiments, the composition comprises about 3 wt % to about 10 wt % PCP. In certain embodiments, the composition comprises about 5 wt % to about 10 wt % PCP. In certain embodiments, the composition comprises about 8 wt % PCP.

In certain embodiments, the composition comprises about 70 wt % to about 95 wt % diesel. In certain embodiments, the composition comprises about 80 wt % to about 95 wt % diesel. In certain embodiments, the composition comprises about 90 wt % to about 95 wt % diesel.

In certain embodiments, the PCP-containing compositions include diesel solvent. In some embodiments, the diesel solvent is American Wood Preservative Association's (AWPA) P9 Type A solvent where the P9 Type A solvent may comprises a "hydrocarbon solvent" and an "auxiliary solvent" which, in combination, satisfy the following physical characteristics as shown in Table 1:

TABLE 1

Physical Characteristics of AWPA P9 Type A Solvent

| Physical Characteristic | Requirement for P9 Type A Solvent |
| --- | --- |
| Distillation | at least 50% at 490° F. (254° C.) |
| | at least 90% at 585° F. (307° C.) |
| Viscosity at 100° F. (38° C.) | at least 37.5 Saybolt Universal Seconds (SUS) |
| Flash Point | at least 150° F. (66° C.) |
| PCP solvency | at least 10 grams of PCP dissolve in 90 grams of whole oil |
| | the oil fraction that is un-distilled above 260° C. dissolves at least 6 grams of PCP per 100 mL oil |
| Water and sediment | at or below 5,000 ppm |
| Specific gravity | at least 0.91 |

"Hydrocarbon solvents" are solvent fractions derived from crude petroleum or high temperature coal tar by common refining processes such as distillation separation, extraction, or by catalytic or thermal rearrangement of the carbon-hydrogen structure of the hydrocarbons of such solvent fractions. In certain embodiments, the hydrocarbon solvent comprises diesel. As used herein, the term "hydrocarbon solvent" does not include biodiesel.

As used herein, the term "auxiliary solvents" or "co-solvents" include hydrocarbon moieties derived from petroleum products or agricultural sources, with the provision that the auxiliary solvent is not biodiesel. The auxiliary solvent is generally blended with the hydrocarbon solvent to improve its physical characteristics.

Biodiesel, which is substantially excluded from some embodiments of the compositions described herein, generally comprises hydrocarbon compounds, predominantly a mixture of saturated and unsaturated $C_{10}$-$C_{22}$ hydrocarbons, other natural products and processing byproducts. It has been found that the saturated $C_{10}$-$C_{22}$ hydrocarbons, in particular and the other natural products and processing byproducts of biodiesel are not effective odor-suppressants. Thus, the compositions described herein, comprising relatively pure forms of unsaturated fatty esters are more effective at suppressing odor than compositions comprising biodiesel.

In certain embodiments, the auxiliary solvent comprises an aromatic solvent such as xylenes. In certain embodiments, the auxiliary solvent comprises naphtha. In certain embodiments, the auxiliary solvent comprises an alcohol. In certain embodiments, the auxiliary solvent comprises an ether. In certain embodiments, the auxiliary solvent excludes biodiesel.

In certain embodiments, the AWPA P9 Type A solvent comprises a hydrocarbon solvent and an auxiliary solvent, where the hydrocarbon solvent comprises diesel and the auxiliary solvent comprises biodiesel. In certain embodiments, the hydrocarbon solvent comprises diesel and the auxiliary solvent comprises soy methyl esters (SME).

In certain embodiments, the AWPA P9 Type A solvent is about 50 wt % to about 99 wt % diesel and about 1 wt % to about 50 wt % biodiesel. In other embodiments, the AWPA P9 Type A solvent is about 70 wt % to about 80 wt % diesel and about 20 wt % to about 30 wt % biodiesel. In certain embodiments, the AWPA P9 Type A solvent is about 75 wt % diesel and about 25 wt % biodiesel. In certain embodiments, the biodiesel comprises soy methyl esters (SME).

In some embodiments, any one of the creosote-based or PCP/diesel-based compositions described herein is substantially free of biodiesel. In some embodiments, any one of the creosote-based or PCP/diesel-based compositions described herein is substantially free of $C_{10}$-$C_{50}$ saturated fatty esters.

In some embodiments, the composition comprises 3 wt % to about 10 wt % of the one or more $C_{10}$-$C_{50}$ unsaturated fatty esters.

Unsaturated Fatty Esters

The creosote-based or PCP/diesel-based compositions described herein one or more $C_{10}$-$C_{50}$ unsaturated fatty esters. In some embodiments, the composition comprises 1-30 wt %, 1-20 wt %, 1-10 wt %, 1-8 wt %, 1-5 wt % of the one or more $C_{10}$-$C_{50}$ unsaturated fatty esters. In some embodiments, the composition comprises 1, 2, 3, 4, 5, 6, 7, 8, 9, 10, 11, 12, 13, 14, 15, 16, 17, 18, 19 or 20 wt % of the one or more $C_{10}$-$C_{50}$ unsaturated fatty esters specified herein.

In some embodiments, the $C_{10}$-$C_{50}$ unsaturated fatty esters comprises one or more monounsaturated fatty esters. In some embodiments, the $C_{10}$-$C_{50}$ unsaturated fatty esters comprise one or more polyunsaturated fatty esters. In some embodiments, the $C_{10}$-$C_{50}$ unsaturated fatty esters are $C_{18}$-$C_{22}$ unsaturated fatty esters. In some embodiments, the $C_{10}$-$C_{50}$ unsaturated fatty esters are $C_{30}$-$C_{50}$ unsaturated fatty esters. The unsaturated fatty esters described herein can be made from the representative unsaturated fatty acids shown in the tables below.

TABLE 2

Monounsaturated fatty acids

| Common name | Lipid name | Chemical name |
| --- | --- | --- |
| palmitoleic acid | (16:1 n-7) | 9-cis-hexadecenoic acid |
| cis-vaccenic acid | (18:1 n-7) | (Z)-octadec-11-enoic acid |
| trans-vaccenic acid | (18:1 n-7) | (E)-octadec-11-enoic acid |
| oleic acid | (18:1 n-9) | (Z)-octadec-9-enoic acid |

TABLE 3

Omega-3 polyunsaturated fatty acids

| Common name | Lipid name | Chemical name |
| --- | --- | --- |
| Hexadecatrienoic acid (HTA) | 16:3 (n-3) | all-cis 7,10,13-hexadecatrienoic acid |
| Alpha-linolenic acid (ALA) | 18:3 (n-3) | all-cis-9,12,15-octadecatrienoic acid |
| Stearidonic acid (SDA) | 18:4 (n-3) | all-cis-6,9,12,15,-octadecatetraenoic acid |
| Eicosatrienoic acid (ETE) | 20:3 (n-3) | all-cis-11,14,17-eicosatrienoic acid |
| Eicosatetraenoic acid (ETA) | 20:4 (n-3) | all-cis-8,11,14,17-eicosatetraenoic acid |
| Eicosapentaenoic acid (EPA, Timnodonic acid) | 20:5 (n-3) | all-cis-5,8,11,14,17-eicosapentaenoic acid |
| Heneicosapentaenoic acid (HPA) | 21:5 (n-3) | all-cis-6,9,12,15,18-heneicosapentaenoic acid |
| Docosapentaenoic acid (DPA, Clupanodonic acid) | 22:5 (n-3) | all-cis-7,10,13,16,19-docosapentaenoic acid |
| Docosahexaenoic acid (DHA, Cervonic acid) | 22:6 (n-3) | all-cis-4,7,10,13,16,19-docosahexaenoic acid |
| Tetracosapentaenoic acid | 24:5 (n-3) | all-cis-9,12,15,18,21-tetracosapentaenoic acid |
| Tetracosahexaenoic acid (Nisinic acid) | 24:6 (n-3) | all-cis-6,9,12,15,18,21-tetracosahexaenoic acid |

TABLE 4

Omega-6 polyunsaturated fatty acids

| Common name | Lipid name | Chemical name |
| --- | --- | --- |
| Linoleic acid | 18:2 (n-6) | all-cis-9,12-octadecadienoic acid |
| Gamma-linolenic acid (GLA) | 18:3 (n-6) | all-cis-6,9,12-octadecatrienoic acid |
| Eicosadienoic acid | 20:2 (n-6) | all-cis-11,14-eicosadienoic acid |
| Dihomo-gamma-linolenic acid (DGLA) | 20:3 (n-6) | all-cis-8,11,14-eicosatrienoic acid |
| Arachidonic acid (AA) | 20:4 (n-6) | all-cis-5,8,11,14-eicosatetraenoic acid |
| Docosadienoic acid | 22:2 (n-6) | all-cis-13,16-docosadienoic acid |
| Adrenic acid | 22:4 (n-6) | all-cis-7,10,13,16-docosatetraenoic acid |
| Docosapentaenoic acid (Osbond acid) | 22:5 (n-6) | all-cis-4,7,10,13,16-docosapentaenoic acid |
| Tetracosatetraenoic acid | 24:4 (n-6) | all-cis-9,12,15,18-tetracosatetraenoic acid |
| Tetracosapentaenoic acid | 24:5 (n-6) | all-cis-6,9,12,15,18-tetracosapentaenoic acid |

TABLE 5

Omega-9 mono- and polyunsaturated fatty acids

| Common name | Lipid name | Chemical name |
| --- | --- | --- |
| Oleic acid[†] | 18:1 (n-9) | cis-9-octadecenoic acid |
| Eicosenoic acid[†] | 20:1 (n-9) | cis-11-eicosenoic acid |
| Mead acid | 20:3 (n-9) | all-cis-5,8,11-eicosatrienoic acid |
| Erucic acid[†] | 22:1 (n-9) | cis-13-docosenoic acid |
| Nervonic acid[†] | 24:1 (n-9) | cis-15-tetracosenoic acid |

[†]Monounsaturated

TABLE 6

Other fatty acids having two or more conjugated double bonds

| Common name | Lipid name | Chemical name |
|---|---|---|
| Conjugated Linoleic Acids (two conjugated double bonds) | | |
| Rumenic acid | 18:2 (n-7) | 9Z,11E-octadeca-9,11-dienoic acid |
|  | 18:2 (n-6) | 10E,12Z-octadeca-9,11-dienoic acid |
| Conjugated Linolenic Acids (three conjugated double bonds) | | |
| α-Calendic acid | 18:3 (n-6) | 8E,10E,12Z-octadecatrienoic acid |
| β-Calendic acid | 18:3 (n-6) | 8E,10E,12Z-octadecatrienoic acid |
| Jacaric acid | 18:3 (n-6) | 8E,10E,12Z-octadecatrienoic acid |
| α-Eleostearic acid | 18:3 (n-5) | 9Z,11E,13E-octadeca-9,11,13-trienoic acid |
| β-Eleostearic acid | 18:3 (n-5) | 9Z,11E,13E-octadeca-9,11,13-trienoic acid |
| Catalpic acid | 18:3 (n-5) | 9Z,11E,13E-octadeca-9,11,13-trienoic acid |
| Punicic acid | 18:3 (n-5) | 9Z,11E,13E-octadeca-9,11,13-trienoic acid |
| Other | | |
| Rumelenic acid | 18:3 (n-3) | 9E,11Z,15E-octadeca-9,11,15-trienoic acid |
| α-Parinaric acid | 18:4 (n-3) | 9E,11Z,13Z,15E-octadeca-9,11,13,15-tetraenoic acid |
| β-Parinaric acid | 18:4 (n-3) | all trans-octadeca-9,11,13,15-tretraenoic acid |
| Bosseopentaenoic acid | 20:5 (n-6) | 5Z,8Z,10E,12E,14Z-eicosanoic acid |

TABLE 7

Other Polyunsaturated fatty acids

| Common name | Lipid name | Chemical name |
|---|---|---|
| Pinolenic acid | 18:3 (n-6) | (5Z,9Z,12Z)-octadeca-5,9,12-trienoic acid |
| Podocarpic acid | 20:3 (n-6) | (5Z,11Z,14Z)-eicosa-5,11,14-trienoic acid |

TABLE 8

Dimeric Unsaturated Fatty Acids

| Structure | Chemical name |
|---|---|
| [structure] | (Z)-9-((E)-non-3-enyl)-10-((E)-non-3-enylidene)octadecanedioic acid |
| [structure] | (E)-8,8'-(5-hexyl-6-(oct-2-enyl)cyclohex-3-ene-1,2-diyl)dioctanoic acid |
| [structure] | 8,8'-(6-butyl-7-hexyl-1,2,4a,5,6,7-hexahydronaphthalene-1,2-diyl)dioctanoic acid |

In some embodiments, the $C_{10}$-$C_{50}$ unsaturated fatty esters are esters of a fatty acid selected from the group consisting of Omega-3 fatty acids, Omega-6 fatty acids, Omega-9 fatty acids, dimeric unsaturated fatty acids and combinations thereof.

In some embodiments, the $C_{10}$-$C_{50}$ unsaturated fatty esters are esters of a fatty acid selected from the group consisting of myristoleic acid, oleic acid, palmitoleic acid, (trans) vaccenic acid, hexadecatrienoic acid, linoleic acid, α-linolenic acid, β-linolenic acid, γ-linolenic acid, stearidonic acid, eicosatrienoic acid, eicosatetraenoic acid, eicosapentenoic acid, heneicosapentenoic acid, docosapentenoic acid, docosahexaenoic acid, tetracosapentenoic acid, tetracosahexaenoic acid, sapienic acid, elaidic acid, linoelaidic acid, α-eleostearic acid, β-eleostearic acid, arachidonic acid, erucic acid and combinations thereof.

In some embodiments, $C_{10}$-$C_{50}$ unsaturated fatty esters are esters of a fatty acid selected from the group consisting of: (Z)-9-((E)-non-3-enyl)-10-((E)-non-3-enylidene)octadecanedioic acid; (E)-8,8'-(5-hexyl-6-(oct-2-enyl)cyclohex-3-ene-1,2-diyl)dioctanoic acid; 8,8'-(6-butyl-7-hexyl-1,2,4a,5,6,7-hexahydronaphthalene-1,2-diyl)dioctanoic acid and combinations thereof.

In some embodiments, the unsaturated fatty ester is an ester of a fatty acid that is selected from the group consisting of oleic acid, linoleic acid, linolenic acid, arachidonic acid and combinations thereof. In some embodiments, the unsaturated fatty ester is an ester of linoleic acid.

In some embodiments, the $C_{10}$-$C_{50}$ unsaturated fatty esters consist essentially of esters of the fatty acid(s) recited in any of the embodiments of the composition described herein.

As used herein, the term "substantially free," means, in certain embodiments, less than about 5 wt %, 4 wt %, 3 wt %, 2 wt %, 1 wt %, 0.1 wt %. For example, a composition that is substantially free of biodiesel or saturated fatty acids, includes less than about 5 wt %, 4 wt %, 3 wt %, 2 wt %, 1 wt % or 0.1 wt % of biodiesel or saturated fatty acids.

As used herein, the term "consists essentially of," when described the constituents of a group, means that the group is made up primarily of those constituents and does not include more than about 5 wt %, 4 wt %, 3 wt %, 2 wt %, 1 wt % or 0.1 wt % of other constituents. For example, a unsaturated fatty ester "group" that consist essentially of a linoleic acid "constituent," contains no more than about 5 wt %, 4 wt %, 3 wt %, 2 wt %, 1 wt % or 0.1 wt % of constituents other than linoleic acid.

In some embodiments, the unsaturated fatty ester is a $C_1$-$C_6$ alkyl ester. In some embodiments, the unsaturated fatty ester is a methyl ester. In some embodiments, the unsaturated fatty ester is an ethyl ester. In some embodiments, the unsaturated fatty ester is a mono-glyceride, di-glyceride or tri-glyceride.

In some embodiments, the unsaturated fatty ester comprises one or more monounsaturated fatty esters. In some embodiments, the unsaturated fatty ester comprises one or more polyunsaturated fatty esters. In some embodiments, the unsaturated fatty ester comprises one or more cis-unsaturated fatty esters.

In some embodiments, the unsaturated fatty ester is an ester of a fatty acid that is selected from the group consisting of Omega-3 fatty acids, Omega-6 fatty acids, Omega-9 fatty acids, dimeric unsaturated fatty acids and combinations thereof. In some embodiments, the unsaturated fatty ester is obtained from tall oil fatty acids or esters.

In some embodiments, the unsaturated fatty ester is an ester of a fatty acid that is selected from the group consisting of myristoleic acid, oleic acid, palmitoleic acid, (trans) vaccenic acid, hexadecatrienoic acid, linoleic acid, α-linolenic acid, β-linolenic acid, γ-linolenic acid, stearidonic acid, eicosatrienoic acid, eicosatetraenoic acid, eicosapentenoic acid, heneicosapentenoic acid, docosapentenoic acid, docosahexaenoic acid, tetracosapentenoic acid, tetracosahexaenoic acid, sapienic acid, elaidic acid, linoelaidic acid, α-eleostearic acid, β-eleostearic acid, arachidonic acid, erucic acid and combinations thereof.

In some embodiments, the unsaturated fatty ester is an ester of a fatty acid that is selected from the group consisting of oleic acid, linoleic acid, linolenic acid, arachidonic acid and combinations thereof. In some embodiments, the unsaturated fatty ester is an ester of a fatty acid that is linoleic acid.

The unsaturated fatty esters effective sequester the VOCs of the compositions described herein and reduce the odor of the compositions described herein. In some embodiments, the amount of volatile organic compounds (VOCs) emitted into the atmosphere at 70° C. by the composition is less than 100 ug/m$^3$. In some embodiments, the amount of naphthalene emitted into the atmosphere at 70° C. by the composition is less than 20 ug/m$^3$.

Borates

In some embodiments, the creosote-containing or PCP-containing compositions described herein further comprise a borate compound. In some embodiments, the borate compound is an ester of boric acid.

Borate compounds contain oxoanions of boron in a +3 oxidation state. The simplest borate ion, $BO_3^{3-}$, and its acidic counterpart, boric acid $B(OH)_3$, have trigonal planar structures. Other borates include trigonal $BO_3$ or tetrahedral $BO_4$ structural units, sharing oxygen atoms. A number of polymeric borate ions are known. They may be made by reacting $B(OH)_3$ or $B_2O_3$ with metal oxides. Examples include: diborate $B_2O_5^{4-}$ (e.g., $Mg_2B_2O_5$), triborate $B_3O_7^{5-}$ (e.g., $CaAlB_3O_7$), tetraborate $B_4O_9^{6-}$ (e.g., sodium tetraborate $Na_2B_4O_7 \cdot 10H_2O$), pentaborate $B_5O_6(OH)_4$ (e.g., sodium pentaborate $Na[B_5O_6(OH)_4] \cdot 3H_2O$), and octaborate (e.g., disodium octaborate tetrahydrate, Tim-Bor, $Na_2B_8O_{13} \cdot 4H_2O$).

Borates, such as octaborate, are broad spectrum insecticides commonly used in the treatment of wood. They have the advantage of being readily diffusible into the interior of wood and exhibit low mammalian toxicity. Solid rods of boric acid, for example, are driven into the base of previously installed utility poles to prolong the life of the pole. Once inserted, the boric acid diffuses into the interior of the pole to protect the base region of the pole. However, the installation of boric acid rods is costly and labor intensive because trenches must be dug around the poles, the base must be drilled, and the rods inserted. Replacement boric acid rods must then be reinserted numerous times during the lifetime of the pole. Further, borates are susceptible to leaching and may not adequately protect against soft rot fungi.

In certain embodiments, the any of the compositions described herein has about 0.01 wt % to about 75 wt % of the ester of boric acid. In certain embodiments, the composition has about 0.01 wt % to about 25 wt % of the ester of boric acid. In certain embodiments, the composition has about 1 wt % to about 15 wt % of the ester of boric acid. In other embodiments, the composition has about 1 wt % to about 5 wt % of the ester of boric acid. In certain embodiments, the composition has about 5 wt % of the ester of boric acid. In other embodiments, the composition has about 4 wt % of the ester of boric acid. In certain embodiments, the composition has about 3 wt % of the ester of boric acid. In other embodiments, the composition has about 2 wt % of the ester of boric acid. In certain embodiments, the composition has about 1 wt % of the ester of boric acid. In certain embodiments, the composition has about 0.01 wt % to about 1 wt % of the ester of boric acid. Unless indicated otherwise, all percentages provided throughout this specification are weight percentages (e.g., wt % or w/w %).

A wide variety of esters of boric acid may be used in any of the present compositions, including but not limited to alkanol, alkenol, alkanolamine esters and mixtures of any two or more. For example, in some embodiments, the ester of boric acid is a $C_1$-$C_{22}$ alkanol ester of boric acid. In certain embodiments, the ester of boric acid is a $C_1$-$C_{12}$ alkanol ester of boric acid. In certain embodiments, the ester of boric acid is a $C_1$-$C_6$ alkanol ester of boric acid. In certain embodiments, the ester of boric acid is a straight chain $C_1$-$C_{22}$ alkanol ester of boric acid. In certain embodiments, the ester of boric acid is a branched $C_1$-$C_{22}$ alkanol ester of boric acid. In certain embodiments, the ester of boric acid is a $C_2$-$C_{22}$ alkenol ester of boric acid. In certain embodiments, the ester of boric acid is a $C_2$-$C_{12}$ alkenol ester of boric acid. In certain embodiments, the ester of boric acid is a $C_2$-$C_6$ alkenol ester of boric acid. In certain embodiments, the ester of boric acid is a monoalkanolamine ester of boric acid. Such an ester of boric acid may be prepared, e.g., from a reaction mixture of about 40 wt % to about 80 wt % boric acid, $C_1$-$C_6$ monoalkanolamine, and water.

In certain embodiments, the composition comprising an ester of boric acid in a creosote/unsaturated fatty ester blend or a PCP/unsaturated fatty ester blend is substantially anhydrous. In certain embodiments, the ester of boric acid is substantially anhydrous. In certain embodiments, substantially anhydrous means less than 5 wt % water. In other embodiments, substantially anhydrous means less than 4 wt % water. In certain embodiments, substantially anhydrous means less than 3 wt % water. In other embodiments, substantially anhydrous means less than 2 wt % water. In certain embodiments, substantially anhydrous means less than 1 wt % water. In other embodiments, substantially anhydrous means less than 0.5 wt % water. In certain embodiments, substantially anhydrous means less than 0.1 wt % water. In other embodiments, substantially anhydrous means less than 0.01 wt % water.

In any of the compositions of the present technology, the ester of boric acid may be a monoester, diester, trimester or a mixture of any two or more thereof. For example, a $C_1$-$C_6$ monoalkanolamine ester of boric acid can be a monoester of boric acid, a diester of boric acid, a triester of boric acid or a mixture of any two or more of the foregoing. In certain embodiments, the $C_1$-$C_6$ monoalkanolamine ester is a monoethanolamine ester of boric acid. A $C_1$-$C_6$ monoalkanolamine ester of boric acid is also referred to herein as a "Borate Ester" and comprises any one of the mono, di or tri esters and/or mixtures thereof. In certain embodiments, the monoethanolamine ester of boric acid is prepared and is referred to herein as the "MBE Ester" or "MBE."

The $C_1$-$C_6$ monoalkanolamine ester (e.g., a monoethanolamine or MBE ester of boric acid) is prepared by mixing $C_1$-$C_6$ monoalkanolamine (e.g., monoethanolamine) in an aqueous solution of boric acid and allowing the $C_1$-$C_6$ monoalkanolamine (e.g., monoethanolamine) to react with the boric acid.

The concentration of $C_1$-$C_6$ monoalkanolamine (e.g., monoethanolamine) in the reaction mixture is about 2 wt % to about 43 wt %; the concentration of water in the reaction mixture is about 2 wt % to about 27 wt %; and the concentration of boric acid in the reaction mixture is about 20 wt % to about 80 wt %. Alternatively, the concentration of $C_1$-$C_6$ monoalkanolamine (e.g., monoethanolamine) in the reaction mixture is about 28 wt % to about 38 wt %; the concentration of water in the reaction mixture is about 12 wt % to about 22 wt %; and the concentration of boric acid in the reaction mixture is about 45 wt % to about 70 wt %. In yet another embodiment, the concentration of boric acid in the reaction mixture is about 48 wt % to about 66 wt % with the remainder of the mixture being $C_1$-$C_6$ monoalkanolamine and water, where the wt % of the $C_1$-$C_6$ monoalkanolamine is approximately twice the wt % of the water. The quantity of $C_1$-$C_6$ monoalkanolamine (e.g., monoethanolamine) in the reaction mixture relative to boric acid can be adjusted upward, resulting in greater amounts of di and triester; or downwards, resulting in lesser amounts of di and triester. Because the reaction is exothermic, in certain embodiments, the esterification reaction of boric acid is carried out with cooling. In some embodiments, water is substantially absent from the treatment solution used in the pressure impregnation step. Thus, in certain embodiments, as much water as possible is evaporated away due to the heat that is generated from the exotherm that occurs during the esterification reaction. In some embodiments, the treatment solution used in the pressure impregnation step has greater than or equal to 5 wt % water. In some embodiments, the treatment solution used in the pressure impregnation step has less than 5 wt % water. In some embodiments, the treatment solution used in the pressure impregnation step has less than 2 wt % water. In some embodiments, the treatment solution used in the pressure impregnation step has less than 1 wt % water.

The Borate Ester solution (i.e., the reaction product of boric acid and the $C_2$-$C_6$ alkanolamine, such as MBE prepared from boric acid and ethanolamine) is then blended with a creosote/unsaturated fatty ester blend or a PCP/unsaturated fatty ester blend to form the treatment solution for the pressure impregnation. In some embodiments the Borate Ester solution has greater than or equal to 5 wt % water. In certain embodiments, the Borate Ester solution is substantially water free. In some embodiments the Borate Ester solution has less than 5 wt % water. In some embodiments the Borate Ester solution has less than 4 wt % water. In some embodiments the Borate Ester solution has less than 3 wt % water. In some embodiments the Borate Ester solution has less than 2 wt % water. In some embodiments the Borate Ester solution has less than 1 wt % water. In some embodiments the Borate Ester solution has less than 0.5 wt % water. In some embodiments the Borate Ester solution has less than 0.1 wt % water. In some embodiments the Borate Ester solution is a MBE solution prepared from boric acid and ethanolamine. The temperature of this blending step is not critical, however, the temperature is typically elevated in order to decrease the viscosity of the treatment solution and thereby facilitate the blending and to remove any remaining water present in the Borate Ester solution. As such, the temperature and period of time during which the elevated temperature is maintained is adjusted so that the blend is homogeneously mixed and substantially all water has been removed through evaporation (e.g., greater 95%, greater than 98%, or greater than 99% w/w free of water). Temperatures of about 120 to about 200° F. are commonly used.

In other embodiments, the ester of boric acid is prepared from a reaction mixture of about 50 wt % to about 70 wt %; boric acid, $C_1$-$C_6$ monoalkanolamine, and water. In certain embodiments, substantially all of the water is removed from the ester of boric acid before being added to the composition.

In other embodiments, the ester of boric acid is a $C_1$-$C_6$ monoalkanolamine ester of boric acid. In certain embodiments, the $C_1$-$C_6$ monoalkanolamine ester of boric acid is a monoethanolamine ester of boric acid. In other embodiments, the monoethanolamine ester of boric acid is a mixture of the mono, di, and triester of boric acid.

Borates and PCP are particularly difficult to dissolve in a minimal and economically feasible volume of solvent such as AWPA P9 Type A solvent. Conversely, creosote more readily dissolves borate compounds. Thus, borate ester compositions were developed with improved solubility in PCP/AWPA P9 Type A solvent systems. Further, methods were developed to maintain the solubility of borate esters in PCP/AWPA P9 Type A solvent systems during storage, handling, and while the wood preservative composition is being impregnated into wood.

In one aspect, a composition is provided comprising: an ester of boric acid in a creosote/unsaturated fatty ester blend or a PCP/unsaturated fatty ester blend. In certain embodiments, the composition of the above aspect comprises a sufficient volume of another co-solvent or additive to maintain stability (i.e., solubility) of boron-containing ingredients within the composition. In some embodiments the co-solvent is not biodiesel. In some embodiments, the compositions described herein are substantially free of biodiesel.

In other embodiments, the composition has an open-cup flashpoint of at least 60° C. In certain embodiments, the composition has an open-cup flashpoint of at least 66° C. In open cup devices for the measurement of flash points, the sample is contained in an open cup which is heated, and at intervals a flame is brought over the surface. The measured flash point will actually vary with the height of the flame above the liquid surface. The best known example is the Cleveland open cup (COC).

Alternatively, the flashpoint of the composition may be measured using closed-type testers. There are two types of closed cup testers: non-equilibrium, such as Pensky-Martens where the vapors above the liquid are not in temperature equilibrium with the liquid, and equilibrium, such as Small Scale (commonly known as Setaflash) where the vapors are deemed to be in temperature equilibrium with the liquid. Both of these types the cups are sealed with a lid through which the ignition source can be introduced. Closed cup testers normally give lower values for the flash point than open cup (typically about 5° C. to about 10° C. lower, or about 9° F. to about 18° F. lower) and are generally regarded as an approximation of the temperature at which the vapor pressure reaches the lower flammable limit.

The flash point is an empirical measurement rather than a fundamental physical parameter. The measured value will vary with equipment and test protocol variations, including temperature ramp rate (in automated testers), time allowed for the sample to equilibrate, sample volume, and whether the sample is stirred.

In other embodiments, the composition is a substantially homogenous solution. In certain embodiments, the composition is a substantially homogenous solution at a temperature of about 15° C. to about 35° C. In certain embodiments, the composition is a substantially homogenous solution at a temperature of about 15° C. to about 35° C. for up to one month. In certain embodiments, the composition is a substantially homogenous solution at a temperature of about 15° C. to about 35° C. for up to one week. In certain embodiments, the composition is a substantially homogenous solution at a temperature of about 25° C. In certain embodiments, a solution is deemed a substantially homogenous solution when suspended solids within the solution are equal to or less than 5 wt %. In certain embodiments, suspended solids within the solution are equal to or less than 4 wt %. In certain embodiments, suspended solids within the solution are equal to or less than 3 wt %. In certain embodiments, suspended solids within the solution are equal to or less than 2 wt %. In certain embodiments, suspended solids within the solution are equal to or less than 1 wt %. In certain embodiments, suspended solids within the solution are equal to or less than 0.5 wt %. In certain embodiments, suspended solids within the solution are equal to or less than 0.25 wt %. In certain embodiments, suspended solids within the solution are equal to or less than 0.1 wt %.

In another aspect, wood is provided, where the wood is coated with or immersed in a composition according to any of the above embodiments. In certain embodiments, the wood is a utility pole. In certain embodiments, the wood is a railroad tie. In certain embodiments, the wood is a dimensional timber.

Odor Suppression and the Sequestration of VOCs

In another aspect, a method is provided of minimizing odor in treated wood, comprising the steps of: a) immersing the wood in the treatment solution comprising any of the compositions described herein; and b) pressure impregnating the immersed wood above 1 atm (101.325 kPa).

In some embodiments of the method, the treatment solution comprises any one of the creosote-based or PCP/diesel-based compositions described herein one or more $C_{10}$-$C_{50}$ unsaturated fatty esters. In some embodiments of the method, the composition comprises 1-30 wt %, 1-20 wt %, 1-10 wt %, 1-8 wt %, 1-5 wt % of the one or more $C_{10}$-$C_{50}$ unsaturated fatty esters. In some embodiments, the composition comprises 1, 2, 3, 4, 5, 6, 7, 8, 9, 10, 11, 12, 13, 14, 15, 16, 17, 18, 19 or 20 wt % of the one or more $C_{10}$-$C_{50}$ unsaturated fatty esters specified herein.

In some embodiments of the method, $C_{10}$-$C_{50}$ unsaturated fatty esters are esters of a fatty acid selected from the group consisting of: (Z)-9-((E)-non-3-enyl)-10-((E)-non-3-enylidene)octadecanedioic acid; (E)-8,8'-(5-hexyl-6-(oct-2-enyl)cyclohex-3-ene-1,2-diyl)dioctanoic acid; 8,8'-(6-butyl-7-hexyl-1,2,4a,5,6,7-hexahydronaphthalene-1,2-diyl) dioctanoic acid and combinations thereof.

In some embodiments of the method, the unsaturated fatty ester is an ester of a fatty acid that is selected from the group consisting of oleic acid, linoleic acid, linolenic acid, arachidonic acid and combinations thereof. In some embodiments, the unsaturated fatty ester is an ester of linoleic acid.

In some embodiments of the method, the $C_{10}$-$C_{50}$ unsaturated fatty esters consist essentially of esters of the fatty acid(s) recited in any of the embodiments of the composition described herein.

In some embodiments of the method, the amount of volatile organic compounds (VOCs) emitted into the atmosphere at 70° C. by the composition is less than 100 ug/m$^3$. In some embodiments of the method, the amount of naphthalene emitted into the atmosphere at 70° C. by the composition is less than 20 ug/m$^3$.

Methods of Treating Wood

In another aspect, a method of treating wood is provided comprising the steps of: immersing the wood in the treatment solution comprising the composition of any of the above embodiments; and pressure impregnating the immersed wood above 1 atm (101.325 kPa); which cause the release of boron from the $C_1$-$C_6$ monoalkanolamine ester of boric acid and which cause the boron to migrate into the interior of the wood.

In certain embodiments, the method is a one-step process for treating wood to prevent or reduce insect or microbial decay.

In some embodiments of the method, the treatment solution comprises any one of the creosote-based or PCP/diesel-based compositions described herein one or more $C_{10}$-$C_{50}$ unsaturated fatty esters. In some embodiments of the method, the composition comprises 1-30 wt %, 1-20 wt %, 1-10 wt %, 1-8 wt %, 1-5 wt % of the one or more $C_{10}$-$C_{50}$ unsaturated fatty esters. In some embodiments, the composition comprises 1, 2, 3, 4, 5, 6, 7, 8, 9, 10, 11, 12, 13, 14, 15, 16, 17, 18, 19 or 20 wt % of the one or more $C_{10}$-$C_{50}$ unsaturated fatty esters specified herein.

In some embodiments of the method, $C_{10}$-$C_{50}$ unsaturated fatty esters are esters of a fatty acid selected from the group consisting of: (Z)-9-((E)-non-3-enyl)-10-((E)-non-3-enylidene)octadecanedioic acid; (E)-8,8'-(5-hexyl-6-(oct-2-enyl)cyclohex-3-ene-1,2-diyl)dioctanoic acid; 8,8'-(6-butyl-7-hexyl-1,2,4a,5,6,7-hexahydronaphthalene-1,2-diyl) dioctanoic acid and combinations thereof.

In some embodiments of the method, the unsaturated fatty ester is an ester of a fatty acid that is selected from the group consisting of oleic acid, linoleic acid, linolenic acid, arachidonic acid and combinations thereof. In some embodiments, the unsaturated fatty ester is an ester of linoleic acid.

In some embodiments of the method, the $C_{10}$-$C_{50}$ unsaturated fatty esters consist essentially of esters of the fatty acid(s) recited in any of the embodiments of the composition described herein.

The disclosed one-step process is more convenient than the two step "envelope" treatment process that is common in the industry for treating wood. In the two step treatment process, the wood is first immersed in a solution and set aside for about six weeks under cover, thereby allowing the solution to diffuse throughout the wood. This first step is followed by a second step, treatment of the solution-infused wood with, for example, creosote, to form a hydrophobic envelope around the infused wood. This second step, the creosote envelope, prevents leaching of the solution from the wood.

Thus, an improved one-step process was developed. To carry out the disclosed one-step processes, the wood being treated to reduce insect and/or microbial decay is immersed in the treatment solution and subjected to conditions that cause solution to migrate into the interior of the wood. If boron-containing solutions are used, the boron is thus transferred into the wood from the carrier solution. The transferred boron reacts quickly to form the boric acid equivalent ($B_2O_3$). This boric acid equivalent is exchanged with oxygen containing ligands, including water, within the wood. The boron moves from the solvent in response to the higher moisture content in the core of the wood and the polar environment at the core of the heartwood. The boric acid equivalent migrates primarily as $B_2O_3$ but may also react with the numerous wood sugars, tannins, acids, and natural decay resistant chemicals such as tropolones and stilbenes to form numerous borate complexes. The disclosed one-step process is more convenient and economical than the conventional two-step process to treat wood.

For example, pressure impregnation is suitable for use in the disclosed one-step process. Pressure impregnation is merely used in the second step of the prior two-step process, during the application of an envelope coating of preservative to the wood being treated. Alternatively, if boron-containing solutions are used in the disclosed one-step process, pressure impregnation is used to both (a) apply the envelope coating of Borate Ester in solvent, and (b) to cause the Borate Ester to decompose and release boron and to cause the released boron to migrate into the interior of the wood.

Pressure impregnation refers to subjecting wood that is immersed in the treatment solution of Borate Ester and solvent, to elevated temperature and pressure for a period of time sufficient to achieve release of boron and migration of the released boron throughout the interior of the wood. The disclosed methods thereby achieve a sufficient concentration of boron within the wood to reduce insect and microbial degradation. Suitable concentrations of boron in the interior of the wood are at least 0.05 pounds per cubic foot (pcf) of Boric Acid Equivalent (BAE) of $B_2O_3$. In certain embodiments, suitable concentrations of boron in the interior of the wood are at least 0.11 pcf of BAE of $B_2O_3$. The precise temperature and pressure can vary according to the thickness and type of wood and length of the treatment time. The person of ordinary skill will be able to determine suitable parameters to achieve a suitable concentration and distribution of boron by monitoring the migration of the boron throughout the interior of the wood by, for example, atomic absorption. Alternatively, argon plasma screening with AWPA boron stain, can be used to confirm presence or absence of boron in the wood (AWPA A3-08-17, 2010).

Treatment parameters can then be adjusted accordingly. Commonly used conditions for the pressure impregnation of borate ester include a pressure of about 100 psi to about 160 psi and a temperature of about 120° F. to about 170° F. (49° C. to about 77° C.). Alternative conditions include a pressure of about 130 psi to about 160 psi and a temperature of about 120° F. to about 150° F. (49° C. to about 66° C.). In certain embodiments, the treatment time is at least 10 minutes. In certain embodiments, the treatment time is about 10 minutes to about 10 hours. In certain embodiments, the treatment time is about 20 minutes to about five hours.

The pressure impregnation is carried out in a pressure vessel. Exemplary pressure vessels include cylindirical retorts that are 5 feet to 8 feet in diameter, with lengths up to 200 feet, which allow for the uniform application of temperature, air, fluid pressure, and vacuum. The wood may be placed into the retort on a small railcar or tram. A working solution tank is used to fill the cylinder with the wood present under various pressure and temperature conditions. The retort holds the wood immersed in the chosen treating solution and allows for control of pressure through fluid pumps and air compressors, temperature with heat exchange coils, and vacuum with liquid ring pumps. These systems are designed to give uniform conditions throughout the volume of the retort so that all areas of the wood are subjected to equal temperature and pressure conditions. Pressure vessels are commercially available from any large steel fabrication facility. Regulations for their design vary from state to state and country to country.

For example, the wood may be treated by loading it into a pressure cylinder, where it is given initial air pressure (e.g., about 138 kPa to about 500 kPa) to fill the wood cells with air. The cylinder is then filled with preservative, which has optionally been preheated (e.g., approximately 90° C.), while using a controlled venting procedure to maintain the pressure in the wood cells. A desired fluid pressure of the preservative is reached (e.g., approximately 1000 kPa) and maintained for several hours depending on the wood species. A "pumping out" of the pressure cylinder then occurs and the "gross retention" of preservative within the wood is determined. If this gross retention is found to be within an acceptable range, a vacuum is applied in order to remove any additional free preservative product. At the end of this process there is a "net retention" of preservative. A final steaming can optionally be performed to clean the wood with a short terminal vacuum. The wood can then be bored as per Canadian Standards Association (CSA) specifications and a pass or fail designation is determined based on penetration and retention of preservative within a specified zone of the wood.

Methods of treating wood as described herein may include any equipment which is commonly available to the skilled artisan: a pressure cylinder, heating source, working tank, storage tank, and a mix tank. This equipment may be automated. The "pressure cylinder" is a long cylindrical tube which contains the wood and preservative mixture and is designed to handle pressures of up to 2500 kPa. A "heat source" allows for maintenance of elevated temperatures within the pressure cylinder and any of the tanks, provides heat for post pressure steaming, and/or to "dry" the wood by boiling it in preservative solution. A "working tank" generally maintains 7-9% of the constituents of the compositions described herein. This tank is generally used to empty and fill the pressure cylinder. A "storage tank" generally stores diesel solvent or creosote and feeds this into the "mix tank" where constituents of the compositions described herein are mixed.

Following pressure impregnation, the wood is separated from the treatment solution. When the process is carried out in a pressure vessel, this is typically accomplished by releasing the pressure and pumping the treatment solution out of the pressure vessel. However, any other suitable means of separating a solid from a liquid can be used, including filtration or centrifugation.

In one embodiment, the cylinder is pressurized with air before it is filled with the treatment solution. This step is referred to herein as "Pretreatment Pressurization." Suitable pressures range from atmospheric pressure to 75 psi. Alternatively, the pressure ranges from 0-25 psi. The Pretreament Pressurization typically lasts from about 10 minutes to about 10 hours. Alternatively, the Pretreatment Pressurization lasts from about 10 minutes to about 3 hours. In another embodiment, the Pretreatment Pressurization lasts from about 20 minutes to about one hour. Following Pretreatment Pressurization, the pressure is maintained while the wood is immersed in the treatment solution for pressure impregnation.

Following the pressure impregnation and separation of the wood from the treatment solution, the wood can be subjected to an expansion bath. An expansion bath is used to minimize leaching and bleeding after treatment and to remove excess preservative from the surface of the wood. Bleeding refers to the flow of preservative solution from the interior of the wood to the surface of the wood. Leaching, which comprises bleeding, refers to the runoff of excess preservative solution from the surface of the wood to the surrounding environment.

Subjecting the wood to an expansion bath refers to immersing the wood in a higher temperature oil and subjecting the oil and immersed wood to elevated temperatures, typically a temperature higher than what was used for the pressure impregnation, typically from about 10° F. to about 40° F. higher; alternatively from about 10° F. to about 20° F. higher. Temperatures of about 140° F. to about 180° F. (about 60° C. to about 82° C.) are commonly used, alternatively from about 130° F. to about 160° F. (about 54° C. to about 71° C.). The duration of exposure of the expansion bath is at least 30 minutes, alternatively from about 0.5 hours to about five hours. In another embodiment, the duration of the expansion bath is from about one to two hours. Examples of suitable high temperature oils include the oils used in the pressure impregnation (e.g., creosote or AWPA P9 Type A solvent with or without PCP, each having unsaturated fatty esters). For example, the oil mixture used for the pressure impregnation can be conveniently used for the expansion by adjusting the temperature upwards. When the expansion bath treatment is completed, the oil is separated from the wood. When the process is carried out in a pressure cylinder, the oil is typically pumped out of the apparatus. Other suitable separation methods can also be used, e.g., filtration. The separation of the oil from the wood is considered herein to be part of the expansion bath.

The expansion bath treatment and separation of the oil (e.g., creosote or AWPA P9 Type A solvent with or without PCP, each having unsaturated fatty esters) from the treated wood is typically followed by vacuum treatment to remove residual liquid. The final vacuum is carried out at pressures of least 10 inches of mercury and typically about 15 to about 40 inches, more commonly about 20 to about 28 inches of mercury. The duration of the vacuum treatment is for at least 15 minutes, alternatively from about 0.5 to about ten hours, and in another embodiment from about 0.5 to about five hours, and in another embodiment from about 0.5 to about two hours.

The Lowry Process and Ruepig Process are well known in the art for applying an envelope coating to wood. Both of the processes are suitable for the disclosed one-step wood treatment process for impregnating wood with the compositions described herein and envelope coating the wood with compositions described herein. The Lowry Process and Ruepig Process are described more fully in the AWPA (AWPA T1-10, 2010).

The prior two-step process often requires the use of wood that is dry, i.e., has a moisture content of about 20 wt % to about 40 wt %. Because the moisture content of most wood is greater than about 20 wt % to about 40 wt %, a drying step is often necessary before the prior two-step process can be employed. Moisture can be removed from wood by, for example, immersing the wood in oil at elevated temperature under vacuum, e.g., at around 180° F. at 24 inches Hg. While the disclosed process can readily treat "dry" wood, one advantage of the disclosed one-step process compared with the prior two-step process is that wood does not need to be rigorously dried in order to be treated by the disclosed one-step process. Specifically, the disclosed one-step process can also be used to treat wood that is "semi dry" (i.e., a moisture content of about 40 wt % to about 70 wt %) and "wet" (i.e., a moisture content above 70% wt %). Moreover, the disclosed process is not limited to any particular type of wood. Examples of wood that can be used in the disclosed process include, but are not limited to, Pine (e.g., Red Pine, Jack Pine, Southern Yellow Pine, Lodgepole Pine), Fir (e.g., Douglas Fir), Western Red Cedar, Spruce, Eastern and Western Hemlock, and hardwoods (e.g., Oak). Wood is commonly in the form of a cant when treated according to the disclosed process. A cant is the square section of timber that follows the removal of the outer bark. In certain embodiments of the method, the treatment reduces insect and/or microbial decay in the wood.

In other embodiments of the method, the pressure impregnation is carried out at a pressure of about 100 psi to about 160 psi (689 kPa to about 1,103 kPa) and a temperature of about 120° F. to about 170° F. (about 49° C. to about 77° C.). In certain embodiments of the method, the pressure is applied gradually at a rate of about 1 psi/min to about 20 psi/min (about 7 kPa/min to about 138 kPa/min). In certain embodiments of the method, the pressure is applied gradually at a rate of about 1 psi/min to about 5 psi/min (about 7 kPa/min to about 34 kPa/min).

In other embodiments, the method further comprises separating the wood from the treatment solution after the pressure impregnation. In certain embodiments, the method further comprises separating the wood from the treatment solution after the pressure impregnation; and exposing the wood to an expansion bath. In other embodiments, the method further comprises exposing the wood to a vacuum below 1 atm (101.325 kPa) after completion of the expansion bath. In certain embodiments of the method, the vacuum is applied gradually at a rate of about 1 psi/min to about 5 psi/min (about 7 kPa/min to about 34 kPa/min).

In certain embodiments of the method, the wood is a mixed softwood cant. In other embodiments of the method, the wood is a mixed hardwood cant. In other embodiments of the method, the wood is a round utility pole with the outer bark removed. In other embodiments of the method, the wood is a vascular cambium. In certain embodiments of the method, the moisture content of the wood is greater than 40 wt %. In other embodiments of the method, the pressure impregnation is carried out according to the Lowry or Rueping process.

In another aspect, wood is provided, where the wood is treated according to any of the above embodiments of the method. In certain embodiments, the wood is a utility pole. In certain embodiments, the wood is a railroad tie. In certain embodiments, the wood is a dimensional timber.

The invention is illustrated by the following examples which are not intended to be limiting in any way.

EXAMPLES

Example 1

Odor Suppression

Head space analysis testing was used to measure the quantity of VOCs emitted by the compositions described herein. Head space analysis is a technique for using gas chromatography for quantifying the vapors in the gas above the compositions described herein. The procedure involves the extraction of a volume of the equilibrium gas over the sample (usually about 10 ml) by a syringe through a vial containing a bed of an appropriate absorbent. The vial is the placed in line with a gas chromatography column, the vial heated and the vaporized sample swept on the column and the components of the gas are separated. This technique includes a GC-MS. 100 ml samples of each of preservative solutions are brought to 10 F above our operating temperatures to determine what gases are present in the atmosphere above the preservative solutions.

In this testing for the efficacy of the odor suppression, naphthalene is used as an indicator for odor. A wood preserving operation emission criteria of 3 $\mu g/m^3$ of naphthalene in the air is established. The levels shown below that are at or below 3 $\mu g/m^3$ of naphthalene are considered passing. This is determined to be the level at which 3 out of residents in the vicinity of the wood treating plant would not be able to detect the odor of naphthalene emissions from the plant.

The results are expressed as a percentage reduction of naphthalene from the starting solution.

TABLE 9

Measurement of the reduction of naphthalene from creosote

| Additive to Creosote | % Reduction Naphthalene from an Initial Concentration | $\mu g/m^3$ naphthalene | Volume % Used | Solution Observations |
|---|---|---|---|---|
| None (creosote alone) | 0 | 621 | 0 | No change |
| soy biodiesel | 94 | 36 | 35 | Emulsification and sludge present; noticeable reduction in oil viscosity |
| soy biodiesel | 96 | 20 | 45 | Emulsification and sludge present; noticeable reduction in oil viscosity |
| animal tallow biodiesel | 50 | 304 | 45 | White colored globules of fat with smell of decay |
| arachidonic ester | >99 | 2 | 10 | No difference noted in solution or product |
| arachidonic ester | >99 | 5 | 4 | No difference noted in solution or product |
| linoleic, oleic, linolenic and arachidonic esters | >99 | 2 | 10 | No difference noted in solution or product |
| linoleic, oleic, linolenic and arachidonic esters | >99 | 3 | 4 | No difference noted in solution or product |

TABLE 10

Measurement of the reduction of naphthalene from PCP-based solutions

| Additive to PCP/Diesel | % Reduction Naphthalene from an Initial Concentration | $\mu g/m^3$ naphthalene | Volume % Used | Solution Observations |
|---|---|---|---|---|
| none (pure PCP/diesel) | 0 | 297 | 0 | No change |
| soy biodiesel | 93 | 20 | 35 | Emulsification and sludge present noticeable reduction in oil color |
| soy biodiesel | 97 | 9 | 45 | Emulsification and sludge present noticeable reduction in oil color |

TABLE 10-continued

Measurement of the reduction of naphthalene from PCP-based solutions

| Additive to PCP/Diesel | % Reduction Naphthalene from an Initial Concentration | $\mu g/m^3$ naphthalene | Volume % Used | Solution Observations |
|---|---|---|---|---|
| animal tallow biodiesel | 56 | 130 | 45 | White colored globules of fat with smell of decay solution remains dark |
| arachidonic ester | >99 | 3 | 10 | No difference noted in solution or product |
| arachidonic ester | >99 | 5 | 4 | No difference noted in solution or product |
| linoleic, oleic, linolenic and arachidonic esters | >99 | 2 | 10 | No difference noted in solution or product |
| linoleic, oleic, linolenic and arachidonic esters | >99 | 4 | 4 | No difference noted in solution or product |

Example 2

Stability of Creosote-Based or PCP-Based Preservative Solutions Containing Either Biodiesel or Unsaturated Fatty Esters The stability of creosote-based and PCP/diesel-based preservative pollutions, each having either biodiesel or unsaturated fatty ester additives was measured. The biodiesel or unsaturated fatty ester additives esters were mixed into the creosote-based and PCP/diesel-based formulations using a standard magnetic stirring system. The resulting creosote-based formulations were heated to operating temperatures of about 100° C. and then cooled back to storage of about 70° C. The resulting creosote-based formulations were heated to operating temperatures of about 70° C. and then cooled back to storage of about 50° C. The formulations were checked for stratification and/or the formation of sludge at both temperatures. All mixing was done in a standard 2 liter beaker with the volume adjusted to 1.5 liters.

TABLE 11

Stability of creosote formulations having biodiesel or unsaturated fatty esters additives.

| Additive | Mixing result | Stratification after cooling/ observations | Depth of sludge/ stratification (ml) | Percentage sludge or stratified volume |
|---|---|---|---|---|
| Soy biodiesel 40% | well mixed | none/light color | 0 | 0 |
| Animal fat biodiesel 40% | mixed but globules of white present | yes/floating | 500 | 33 |
| Linseed biodiesel 40% | well mixed | yes/light color/floating | 100 | 7 |
| Arachidonic ester | well mixed | none | 0 | 0 |
| Linoleic, oleic, linolenic and arachidonic esters | well mixed | none | 0 | 0 |

TABLE 11-continued

Stability of creosote formulations having biodiesel or unsaturated fatty esters additives.

| Additive | Mixing result | Stratification after cooling/ observations | Depth of sludge/ stratification (ml) | Percentage sludge or stratified volume |
|---|---|---|---|---|
| Linoleic ester | well mixed | none | 0 | 0 |

TABLE 12

Stability of PCP/diesel formulations having biodiesel or unsaturated fatty esters additives.

| Additive | Mixing result | Stratification after cooling/ observations | Depth of sludge/ stratification (ml) | Percentage sludge or stratified volume |
|---|---|---|---|---|
| Soy biodiesel 40% | well mixed | none | 0 | 0 |
| Animal fat biodiesel 40% | mixed but globules of white present | yes/sinking | 600 | 40 |
| Linseed biodiesel 40% | well mixed | none/some emulsion | 60 | 4 |
| Arachidonic ester | well mixed | none | 0 | 0 |
| Linoleic, oleic, linolenic and arachidonic esters | well mixed | none | 0 | 0 |
| Linoleic ester | well mixed | none | 0 | 0 |

Additional stability tests were conducted with treated wood samples over varying moisture contents and species to determine if the application of pressure, temperature, wood extractives and sudden vacuum would cause the solution to have phase changes from liquid to solid. This is referred to as stressing the solution.

Example 3

Properties of the Creosote/Unsaturated Fatty Ester Formulations

Experiments were undertaken to determine that the addition of unsaturated fatty acid esters to creosote did not materially affect the properties of the creosote as per the AWPA 2012 specification P1-P13-09 and P2-09. The Table below compares the physical properties of a creosote formulation with and with out a 10% mixture of linoleic, oleic, linolenic and arachidonic unsaturated fatty methyl esters (1:1:1:1 ratio).

TABLE 13

| P2-09 Standard for Creosote Solution | | | |
|---|---|---|---|
| | Creosote * | Creosote ** | 1:1:1:1 Blend of unsaturated fatty esters (10%) |
| Water Content (% by volume) | >1.5 | >3.0 | >1.5 |
| Material insoluble in Xylene | 3.5 | >4 | >3 |
| Specific Gravity @ 38° C. (compared to Water @15.5° C.) | | | |
| Whole Creosote | <1.080 >1.130 | >1.080 >1.130 | >1.095 |
| Fraction 235-315° C. | <1.025 | >1.025 | >1.025 |
| Fraction 315-355° C. | <1.085 | >1.085 | >1.093 |
| Distillation | | | |
| Up to 210° C. | <5.0 | <5.0 | <4.01 |
| Up to 235° C. | <25.0 | <25.0 | <23.5 |
| Up to 315° C. | >32.0 | >32.0 | <34.6 |
| Up to 355° C. | >52.0 | >52.0 | <54 |

Creosote * is new creosote that has not yet been in contact with wood.
Creosote ** is creosote that has been in contact with wood and the chemicals in wood and has been "stressed"

Example 4

Efficacy Testing of Wood Treated with Creosote/Unsaturated Fatty Ester Formulations or PCP/Unsaturated Fatty Ester Formulations ASTM test fungi in Petri dishes were subjected to Treatment solutions with and without unsaturated fatty esters (linoleic, oleic, linolenic and arachidonic esters as a 1:1:1:1 ratio). The agar plate test method allowed for rapid determinations of antifungal efficacy against wood-degrading strains of concern. The certified cultures were obtained from the American Type Culture Collection (ATCC) and propagated as per the product information sheets:

*Irpex lacteus*: ATCC number 11245, yeast medium Difco 0712 (ATCC medium no. 200)
*Neolentius lepideus*: ATCC number 12653, YM agar Difco 0712 (ATCC medium no. 200)
*Postia poria*: ATCC number 11538, YM agar Difco 0712 (ATCC medium no. 200)
*Pleurotus ostreatus*: ATCC number 32237, YM agar Difco 0712 (ATCC medium no. 200)
*Trametes versicolor*: ATCC number 42462, Hagem's-Modess medium (ATCC medium no. 479)
*Gleoephyllum trabeum*: ATCC number 11539, Potato Dextrose Agar with 0.5% yeast extract (ATCC medium no. 337)

Each plate was then inoculated in a flame induced sterile environment with a 5 mm diameter agar plug fungal colony of those fungi listed. Plates subsequently received surface application of 0.5 ml and 1 ml of creosote, PCP, creosote/unsaturated fatty ester blends and the PCP/unsaturated fatty ester blends; and controls having only the fungal colony. The plates were incubated for 14 days at 30 C and the presence or absence of fungal growth was noted and measured.

The results of agar plate testing showed that the unsaturated fatty esters did not diminish the antimicrobial activity of creosote or PCP. The growth of fungi was completely inhibited by the creosote, PCP, creosote/unsaturated fatty ester blends and the PCP/unsaturated fatty ester blends. Controls showed complete coverage of the plate.

TABLE 14

| Agar Plate Testing | | | | |
|---|---|---|---|---|
| Fungi | Replications | Control | Creosote/10% unsaturated fatty ester blend (1:1:1:1) | PCP/10% unsaturated fatty ester blend (1:1:1:1) |
| 11245 | 7 | FPG | NG | NG |
| 12653 | 7 | FPG | NG | NG |
| 11538 | 7 | FPG | NG | NG |
| 32237 | 7 | FPG | NG | NG |
| 42462 | 7 | FPG | NG | NG |
| 11539 | 7 | FPG | NG | NG |

*FPG—Full growth of Fungi on Plate Agar
**NG—No Growth of Fungi on Plate Agar

Example 5

Soil Block Efficacy Testing

Testing With Soil-Block Cultures: Standard soil block efficacy testing experiments and soil bed testing experiments can be conducted according to the AWPA guidelines.

For example, mixed hardwood blocks (from about 14 mm to about 19 mm) are tested at various weight percentages of creosote; PCP/diesel; creosote/unsaturated fatty ester blends; and PCP/unsaturated fatty ester blends are tested in a five step retention series. Treated blocks are exposed to the destructive species of fungi outlined above for periods of up to 16 weeks at about 25° C. to about 27° C. and about 65% to about 75% relative humidity. Efficacy is evaluated as mass loss on each block, according to method E10-09 in the AWPA 2011 standards.

Example 6

Treating Cycles for Infusing Creosote/Unsaturated Fatty Ester Formulations or PCP/Unsaturated Fatty Ester Formulations Into Softwood Utility Poles Red Pine Dry: Relatively dry Red Pine utility poles are loaded onto trams and placed into a treatment cylinder. The air pressure is kept at atmospheric pressure or increased to approximately 40 psi (276 kPa), with controlled venting, while filling the cylinder with preservative solution of creosote; PCP/diesel; creosote/unsaturated fatty ester blends; or PCP/unsaturated fatty ester blends. The temperature is increased to 150° F. (66° C.). The pressure is then gradually increased to approximately 150 psi (1,034 kPa) over 30 min. The pressure was then gradually released over the next 30 minutes and the preservative (e.g., creosote/unsaturated fatty ester formulations or PCP/unsaturated fatty ester formulation) is pumped from the treatment cylinder. After the preservative is pumped from the treatment cylinder, a vacuum is gradually applied over 20 minutes, reaching the 27 inches of Hg level at the end of the 20 minute period. The vacuum is then released and live steam is injected, to reduce the oil viscosity, for 1 hour at 160° F. (71° C.), followed by a final vacuum for over 30 minutes.

Wet: Moist or wet Red Pine utility poles are placed into the treatment cylinder and only ¾ of the preservative solution was used during the filling step to create an air space. As the oil was heated and a vacuum was applied, moisture from the wet pole is drawn off the top of the cylinder. Heat and vacuum are maintained until the rate of accumulation of water in the steam capture tank is less than 50 gallons per hour. Otherwise, the remaining treatment steps are the same as for dry poles.

Douglas Fir

Dry: Relatively dry Douglas Fir utility poles are loaded onto trams and placed into the treatment cylinder. The air pressure is kept at atmospheric pressure or increased to approximately 60 psi (414 kPa), with controlled venting, while filling the cylinder with preservative solution of creosote; PCP/diesel; creosote/unsaturated fatty ester blends; or PCP/unsaturated fatty ester blends. The temperature is increased to 160° F. (71° C.). The pressure is then gradually increased to approximately 160 psi (1,103 kPa) over 30 min. Pressure is maintained several hours until gross retention of the preservative solution is achieved. The pressure is then gradually released over the next 30 minutes and the preservative is pumped from the treatment cylinder. After the preservative is pumped from the treatment cylinder, a vacuum is gradually applied over 60 minutes, reaching 27 inches of Hg at the end of the 60 minute period. The vacuum is then released and live steam is injected, to reduce the oil viscosity, for 1 hour at 160° F. (71° C.), followed by a final vacuum for over 60 minutes.

Wet: Moist or wet Douglas Fir utility poles are placed into the treatment cylinder and only ¾ of the preservative solution is used during the filling step to create an air space. As the oil is heated and a vacuum was applied, moisture from the wet pole is drawn off the top of the cylinder. Heat and vacuum are maintained until the rate of accumulation of water in the steam capture tank is less than 50 gallons per hour. Otherwise, the remaining treatment steps are the same as for dry poles.

Southern Yellow Pine

Dry: Relatively dry Southern Yellow Pine utility poles are loaded onto trams and placed into the treatment cylinder. The air pressure is kept at atmospheric pressure or increased to approximately 30 psi (207 kPa), with controlled venting, while filling the cylinder with preservative solution of creosote; PCP/diesel; creosote/unsaturated fatty ester blends; or PCP/unsaturated fatty ester blends. The temperature is increased to 150° F. (66° C.). The pressure is then gradually increased to approximately 150 psi (1,034 kPa), over 20 min. The pressure is then gradually released over the next 20 minutes and the preservative is pumped from the treatment cylinder. After the preservative is pumped from the treatment cylinder, a vacuum is gradually applied over 20 minutes, reaching 27 inches of Hg at the end of the 20 minute period. The vacuum is then released and live steam is injected, to reduce the oil viscosity, for 1 hour at 160° F. (71° C.), followed by a final vacuum for over 30 minutes.

Wet: Moist or wet Southern Yellow Pine utility poles are placed into the treatment cylinder and steamed while pulling a vacuum to remove moisture. Otherwise, the remaining treatment steps were the same as for dry poles.

Example 7

Treating Cycles for Infusing Creosote/Unsaturated Fatty Ester Formulations or PCP/Unsaturated Fatty Ester Formulations Into Hardwood Utility Poles Hardwood utility poles are subjected to similar Treatment Cycles with creosote; PCP/diesel; creosote/unsaturated fatty ester blends; and PCP/unsaturated fatty ester blends as those used for Red Pine utility poles. However, an expansion bath is used for one hour at a 10° F. higher temperature, followed by live steaming.

Example 8

Burn Testing

Burn testing is conducted, for example, at the Institute for Combustion Science and Environmental Technology's (IC-SET) gas emissions laboratory in Bowling Green Ky., to confirm that the dioxin and furan levels do not increase upon combustion. Fire retardant properties, which are generally proportional to concentration of boron in the formulation, are also evaluated according to the AWPA specifications.

Example 9

Leaching

The leaching of the poles is tested according to a modified E11-06 AWPA method. Replicates of 8 foot pole sections are leached for a two week periods. Poles treated with creosote; PCP/diesel; creosote/unsaturated fatty ester blends; and PCP/unsaturated fatty ester blends are evaluated to confirm that there is no significance difference between the leaching characteristics of these poles.

Example 10

Mechanical Properties

Mechanical properties of the wood are tested in conjunction with Nova Scotia Power's (NSP) Engineering and Operational Groups. Surface hardness, ease of drilling, gaff penetration for climbing the poles, strength, modulus of elasticity (MOE), and modulus of rupture (MOR) are tested as per the ASTM D1036 standard. The gaff penetration and drilling tests are performed by actual linemen, on installed poles treated with creosote; PCP/diesel; creosote/unsaturated fatty ester blends; or the PCP/unsaturated fatty ester blends. Static bending according the ASTM D1036 testing method is performed in the presence of three Engineers from NSP, and all poles are observed for their deflection upon load indicating higher than acceptable modulus of elasticity and modulus of rupture. For example, a Douglas Fir pole is generally required to take 3700 pounds of force. Poles treated with creosote; PCP/diesel; creosote/unsaturated fatty ester blends; or PCP/unsaturated fatty ester blends are contemplated to withstand an extreme ultimate horizontal breaking force, for example, in the event that an electric line is knocked over.

Example 11

Corrosion Testing

Poles treated with creosote; PCP/diesel; creosote/unsaturated fatty ester blends; or PCP/unsaturated fatty ester blends are contemplated to undergo minimal corrosion, according to results obtained from ASTM designated tests. Immersion corrosion testing (AWPA standard E-12-94) is conducted to determine the susceptibility of galvanized metal hardware in contact with treated wood to corrosion once installed into utility poles that were treated with creosote; PCP/diesel; creosote/unsaturated fatty ester blends; or PCP/unsaturated fatty ester formulations.

This method compares the initial mass of the hardware to that obtained after environmentally accelerated contact with the treated material for a specified period of time. The mass loss is then translated into a projected/anticipated rate of corrosion for that particular metal while in contact with that particular treated product. These tests, using creosote; PCP/diesel; creosote/unsaturated fatty ester blends; or PCP/unsaturated fatty ester blends, are contemplated to show no significant corrosion on galvanized hardware.

Each corrosion simulation is replicated 4 times with 4 bolt clusters for each treatment. Specified AWPA environmental parameters (49±1° C. and 90±1% relative humidity) are applied in accelerated growth chambers for a periods of 240 hours and 480 hours, during which no significant corrosion is contemplated to occur for the above-described treatments.

What is claimed is:

1. A composition comprising:
   i) at least about 85 wt. % creosote; and
   ii) at least about 3 wt. % of a fatty ester component, which comprises greater than 90 wt. % of one or more $C_1$-$C_6$ alkyl esters of $C_{10}$-$C_{50}$ unsaturated fatty acids; and
   iii) at least about 1 wt. % of an ester of boric acid;
   wherein the composition contains less than 2 wt. % water and is a substantially homogenous solution at a temperature of about 15° C. to about 35° C. for up to one month.

2. The composition of claim 1, comprising about 3 to 10 wt % of the fatty ester component and at least about 90 wt % of the creosote.

3. The composition of claim 1, wherein the composition is substantially free of $C_{10}$-$C_{50}$ saturated fatty esters.

4. The composition of claim 1, wherein the composition comprises about 1 to 5 wt. % of the ester of boric acid.

5. The composition of claim 1, wherein the amount of volatile organic compounds (VOCs) emitted into the atmosphere by the composition as measured by head space analysis at 70° C. is less than 100 μg/m³.

6. A composition comprising:
   i) about 1 to 20 wt % pentachlorophenol;
   ii) about 65 to 98 wt % diesel;
   iii) about 1 to 15 wt % of one or more $C_1$-$C_6$ alkyl esters of $C_{10}$-$C_{50}$ unsaturated fatty acids; and
   iv) an ester of boric acid; wherein the composition contains less than 2 wt. % water.

7. The composition of claim 6, wherein the $C_{10}$-$C_{50}$ unsaturated fatty esters comprise one or more polyunsaturated fatty esters.

8. The composition of claim 6, wherein the $C_{10}$-$C_{50}$ unsaturated fatty esters comprise $C_{18}$-$C_{22}$ unsaturated fatty esters.

9. The composition of claim 6, wherein the unsaturated fatty esters comprise methyl esters.

10. The composition of claim 6, comprising about 1 to 15 wt. % of the ester of boric acid.

11. The composition of claim 10, wherein the ester of boric acid comprises a monoethanolamine ester of boric acid.

12. The composition of claim 6, wherein the composition has an open-cup flashpoint of at least 66° C.

13. The composition of claim 6, wherein the composition is a substantially homogenous solution at a temperature of about 15° C. to about 35° C. for up to one month.

14. Wood coated impregnated with the composition according to claim 6.

15. Wood according to claim 14, wherein the wood is a utility pole.

16. Wood according to claim 14, wherein the wood is a railroad tie.

17. A composition comprising:
   i) about 1 to 20 wt. % pentachlorophenol;
   ii) at least about 65 wt. % diesel; and
   iii) a fatty ester component, which comprises one or more $C_1$-$C_6$ alkyl esters of $C_{10}$-$C_{50}$ unsaturated fatty acids; and
   iv) boric acid ester;
   wherein the composition is a substantially homogenous solution at a temperature of about 15° C. to about 35° C. for up to one month; and the composition contains less than 2 wt. % water and no more than 0.25 wt. % suspended solids.

18. The composition of claim 17, wherein the boric acid ester comprises $C_1$-$C_6$ monoalkanolamine ester of boric acid.

19. The composition of claim 17, wherein the composition comprises about 1 to 15 wt. % of the one or more the $C_{10}$-$C_{50}$ unsaturated fatty esters, which comprise methyl esters of $C_{18}$-$C_{22}$ unsaturated fatty acids; and about 1 to 15 wt. % of the boric acid ester, which comprises monoethanolamine ester of boric acid.

20. The composition of claim 17, wherein the composition has an open-cup flashpoint of at least 66° C. and the amount of volatile organic compounds (VOCs) emitted into the atmosphere by the composition as measured by head space analysis at 70° C. is less than 100 μg/m³.

21. The composition of claim 17, wherein the fatty ester component comprises greater than 80 wt % of the one or more $C_{10}$-$C_{50}$ unsaturated fatty esters.

22. A composition comprising:
   i) about 3 to 15 wt. % pentachlorophenol;
   ii) at least about 65 wt. % diesel; and
   iii) about 1 to 15 wt. % of one or more $C_1$-$C_6$ alkyl esters of $C_{10}$-$C_{50}$ unsaturated fatty acids; and
   iv) about 1 to 5 wt. % of a borate compound, which comprises (a) monoethanolamine ester of boric acid and (b) boric acid and/or disodium octaborate tetrahydrate;
   wherein the composition contains less than 2 wt. % water and is a substantially homogenous solution at a temperature of about 15° C. to about 35° C. for up to one month; and the amount of naphthalene emitted into the atmosphere by the composition as measured by head space analysis at 70° C. is less than 20 μg/m³.

23. A composition comprising:
   i) at least about 85 wt % creosote;
   ii) at least about 3 wt. % one or more $C_1$-$C_6$ alkyl esters of $C_{10}$-$C_{50}$ unsaturated fatty acids; and iii) about 1 to 5 wt. % of a borate compound, which comprises (a) monoethanolamine ester of boric acid and (b) boric acid and/or disodium octaborate tetrahydrate;

wherein the composition contains less than 2 wt. % water and is a substantially homogenous solution at a temperature of about 15° C. to about 35° C. for up to one month; and the amount of naphthalene emitted into the atmosphere by the composition as measured by head space analysis at 70° C. is less than 20 μg/m$^3$.

24. A method of treating wood, comprising the steps of:
a) immersing the wood in the treatment solution comprising the composition of claim 1; and
b) pressure impregnating the immersed wood under a pressure above 1 atm (101.325 kPa).

25. The method of claim 24, further comprising c) separating the wood from the treatment solution after the pressure impregnation; d) exposing the wood to an expansion bath; and e) exposing the wood to a vacuum below 1 atm (101.325 kPa) after completion of the expansion bath.

26. Wood treated according to the method of claim 24.

* * * * *

UNITED STATES PATENT AND TRADEMARK OFFICE
CERTIFICATE OF CORRECTION

PATENT NO. : 10,264,794 B2
APPLICATION NO. : 14/769992
DATED : April 23, 2019
INVENTOR(S) : Gordon Murray It is certified that error appears in the above-identified patent and that said Letters Patent is hereby corrected as shown below:

In the Claims

In Claim 14, Column 28, Lines 11-12: insert -- Wood coated or impregnated with the composition according to Claim 6. --

Signed and Sealed this
Thirtieth Day of July, 2019

Andrei Iancu
*Director of the United States Patent and Trademark Office*